(12) United States Patent
Sesic

(10) Patent No.: US 6,517,541 B1
(45) Date of Patent: Feb. 11, 2003

(54) AXIAL INTRAMEDULLARY SCREW FOR THE OSTEOSYNTHESIS OF LONG BONES

(76) Inventor: Nenad Sesic, Prilaz V. Brajkovica 10, HR-102000 Zagreb (HR)

(*) Notice: Subject to any disclaimer, the term of this patent is extended or adjusted under 35 U.S.C. 154(b) by 0 days.

(21) Appl. No.: 09/869,016
(22) PCT Filed: Dec. 22, 1999
(86) PCT No.: PCT/HR99/00033
§ 371 (c)(1), (2), (4) Date: Jun. 22, 2001
(87) PCT Pub. No.: WO00/38586
PCT Pub. Date: Jul. 6, 2000

(30) Foreign Application Priority Data

Dec. 23, 1998 (HR) .......................................... P980637A
Dec. 22, 1999 (HR) .......................................... P990405A

(51) Int. Cl.⁷ .............................................. A61B 17/56
(52) U.S. Cl. ............................ 606/62; 606/64; 606/63
(58) Field of Search ............................ 606/62, 60, 63, 606/64, 65, 66, 67, 68, 73; 623/23.27

(56) References Cited

U.S. PATENT DOCUMENTS

| | | | |
|---|---|---|---|
| 3,783,860 A | * | 1/1974 | Burstein et al. |
| 4,016,874 A | | 4/1977 | Maffei et al. |
| 4,175,555 A | | 11/1979 | Herbert |
| 4,463,753 A | | 8/1984 | Gustilo |
| 5,603,715 A | * | 2/1997 | Kessler |
| 5,620,445 A | * | 4/1997 | Brosnahan et al. |
| 5,626,580 A | | 5/1997 | Brosnahan |
| 5,665,087 A | * | 9/1997 | Huebner |
| 5,713,901 A | * | 2/1998 | Tock |
| 6,319,255 B1 | * | 11/2001 | Grundei et al. |
| 6,322,591 B1 | * | 11/2001 | Ahrens |

FOREIGN PATENT DOCUMENTS

| | | |
|---|---|---|
| DE | 3835682 | 4/1990 |
| EP | 0 321 170 B | 6/1989 |
| EP | 0 441 577 A | 8/1991 |
| EP | 0451932 | 10/1991 |
| HR | P921004A A2 | 6/1996 |
| WO | 9416636 | 8/1994 |
| WO | 9420040 | 9/1994 |
| WO | 96/02202 | 2/1996 |

OTHER PUBLICATIONS

M.E. Mueller; M. Allgower, R. Schneider, H. Willenegger; The Comprehensive Classificationof Fractures of Long Bones, Manual of Internal Fixation, Third Edition, 1991, pp. 118–150, Springer Verlag.

Database WPI, Section PQ, Week 9716 Derwent Publications Ltd., London, GB; AA 97–173344 XP002137669 & JP 09 038106 A (Terumo), Feb. 10, 1997 abstract; figures 1, 4.

* cited by examiner

Primary Examiner—Pedro Philogene
(74) Attorney, Agent, or Firm—Birch, Stewart, Kolasch & Birch, LLP

(57) ABSTRACT

An axial intramedullary screw having a straight cylindrical outer surface for the operative treatment of long bones, the screw having two tips and a screw thread extending between the tips. At each of the tips there is a connection portion for screwdriver. The screw thread is used for cutting into the cortical bone of the medullary canal and due to the screwdriver connection at both ends it can be driven from either end through the cortical bone. This allows a method to be used in which the screw is threaded into one portion of a bone fragment and then after connecting a further bone fragment at the fracture site, screwed in a different direction into that further fragment. The screw also includes a transverse screw hole at one or both ends for the passage of an interlocking transverse screw therethrough.

19 Claims, 3 Drawing Sheets

AXIAL INTRAMEDULLARY SCREW FOR THE OSTEOSYNTHESIS OF LONG BONES

This application is the national phase under 35 U.S.C. §371 of PCT International Application No. PCT/HR99/00033 which has an International filing date of Dec. 22, 1999, which designated the United States of America and was published in English.

BACKGROUND OF THE INVENTION

1. Field of the Invention

This invention relates generally to the wide area of orthopaedic surgery and traumatology and, more particularly, to the operative treatment of fractures of long bones in humans and animals.

2. Description of Related Art

Many different implants are used internationally and in different parts of the world. Among them are different bone screws (cortical, cancellous, malleolar, DHS, DCS etc.), bone plates (straight, angular etc), different types of external fixators and different intramedullary implants (Kuntcher nail, Rush nail, Ender nail, Kirschner wires implanted intramedullary, "gama nail" and, more recently, the interlocking nail). The axial intramedullary screw (AIMS), in accordance with the subject invention and described hereinafter, includes most of the operative indications for all formerly mentioned bone implants (fasteners), and may be used instead of them.

It is logical to compare the axial intramedullary screw (AIMS) with other intramedullary implants (Kuntscher nail, interlocking nail etc. for the osteosynthesis of long bones (humerus, radius, ulna, femur, tibia, fibular, and also metacarpal and metatarsal bones and clavicle). The long bones are emphasized here because fastening two or more bone parts with a single small screw is in wide use. For instance the "Herbert screw" (U.S. Pat. No. 4,175,555) is applied to the small scaphoid bone of the hand, which is composed mainly of cancellous (spongy) bone with little diaphyseal part (without tubular cortical part). Therefore, it is the mechanical principle of osteosynthesis of AIMS which is different. The latter is two-sided, which is not the case with the Herbert screw. The same comment may be mentioned for the differences with Huebner screw (WO 94/16636) with variable pitch, applied also for small cancellous bones. The same comment is also true for the compressional screw (WO 94/20040) which compresses the separated bone pieces (not long bone parts to one unit), and it is not applied intramedullary like the Kuntscher nail. In addition, they are all too small, with sizes like standardized (ISO) cortical or cancellous bone screws, for use in fixation of long bones. The current method of treatment of fractures of long bones by intramedullary fixation (Kuntscher nail, interlocking nail etc.) is based on two mechanical principles, gliding and locking. AIMS is more compatible with use for these implants from the point of size, principles of implantation and operative indications. But there is also some differences in basic mechanical principles:

1. Gliding—fragments of the fractured bone are allowed to glide along the implant (Kuntscher nail, Ender and Rush nail) because the friction between the nail and bone is generally small. One form is described in patent application (HR P921004A A2). It is based on the combination of the classical interlocking intramedullary nail and flexible leading screw positioned in the central internal part of the nail. The thread of the central leading screw is smaller than the smaller diameter of the cortical bone and it is in contact with the intramedullary nail. This flexible screw is not in contact with cortical bone (the main mechanical principle of AIMS) and it is not responsible for stability of bone fragments. Also the purpose of this device is distraction (elongation) of the femur and these characteristics are very different from AIMS.

2. Locking—with transverse screws in multi fragmented diaphyseal fractures. There are three functions for this:
   (a) Attainment of axial and rotator stability (interlocking Kuntscher nail, Verrigelungs Nagel);
   (b) Possible compression by transverse screw over central intramedullary nail. The best example is the "gama nail" described in different variations in many patent applications. For instance in EPO 0 441 577 A3 by the name "Intramedullary hip screw" and also in EPO 0 321 170 B1, where term "intramedullary screw" is related to transverse spongeosal screw through the femoral neck with the purpose of compression of the femoral head to a central femoral nail (short Kuntscher nail). These two characteristics are very different from the hereafter described variations of the interlocking AIMS.
   (c) Modular intramedullary nail (WO 96/02202) is composed 2 or 3 parts (nails) connected with conical connections, but it is different from the modular AIMS hereafter described because it is only a nail and not an intramedullary screw.

SUMMARY OF THE INVENTION

The purpose of the AIMS bone implant system in accordance with the subject invention, from the technical point of view, is the same as for other osteosynthetic devices.

It is the object of the present invention, therefore, to maintain relative stability between the fractured bone parts with the purpose of creating optimal conditions for bone healing. During the procedure of application of any osteosynthetic device some basic mechanical principles are used to promote optimal osteosynthesis: namely, (1) Interfragmentary compression (statical and dynamic) by lag screw, plate, external fixator etc.; (2) Gliding (by Kutscher, Rush and Endernail); (3) A combination of the last two principles—for example compression lag screw and neutralization plates; and, (4) Neutralisation, unloading (neutral support without compression or distraction)—used in the application of interlocking nails in multi fragmented fractures.

The AIMS system may be applied by the use of all the aforementioned mechanical principles depending on the type of fracture or local biomechanical needs.

In one aspect of the invention, there is provided an axial intramedullary screw having a straight cylindrical outer surface for the operative treatment of long bones, the screw having two tips and a screw thread extending between the tips. At each of the tips there is a connection portion for a screwdriver. The screw thread is used for cutting into the cortical bone of the medullary canal and due to the screwdriver connection at both ends it can be driven from either end through the cortical bone. This allows a method to be used in which the screw is threaded into one portion of a bone fragment and then after connecting a further bone fragment at the fracture site, screwed in a different direction into that further fragment.

In another aspect of the invention, the screw also includes a transverse screw hole at one or both ends for the passage of an interlocking transverse screw therethrough.

BRIEF DESCRIPTION OF THE DRAWINGS

The following detailed description of the invention will be more readily understood when considered in connection with the accompanying drawing figures which are provided by way of illustration and not limitation, and wherein.

DETAILED DESCRIPTION

In distinction to all other intramedullary implants (Kuntscher and interlocking nail), the AIMS system, in accordance with the subject invention, does not create axial and bending stability using the mechanical principles formerly described (gliding and locking). The characteristic of the subject AIMS system is that axial and bending stability is attained through neutralization (unloading) by wide contact between threads of the AIMS cutting into the internal cortex of all fragments of the fractured bone. For the creation of rotatory stability it is possible also to apply one or more interlocking screws (FIG. 4C and FIG. 6–FIG. 11). Therefore, it is possible to use AIMS for multi fragmented fractures and for the same indications as the Interlocking (Kuntscher) nail. As distinguished from other intramedullary implants AIMS is very rigid. The principles of the application of AIMS are very similar to other intramedullary implants, but it is also distinguished from them in some important features: namely, (1). AIMS is connected by the thread to the internal cortical part of the long tubular bone. This feature creates a very high degree of stability among the fractured parts of the bone, much higher than with other osteosynthesis devices and implants. AIMS transfers forces of load directly from proximal to distal bone fragments over a wide circumferential contact area. The same principle of load transmission over centrally positioned implants is also the case with the interlocking nail, but there is stress concentration in the area of the interlocking screws and the nail is more flexible and not as still as with the AIMS. As there are different intramedullary bone diameters, there are different diameters of AIMS ( 1–18 mm), different lengths, pitches of the thread, types of the thread (cortical, cancellous, metric, etc.). Despite this, in some cases there is a need for pre-reaming the medullary canal for adaptation before application of the correct AIMS—self-tapping or non-self-tapping (required a predrilled hole and cutting with a tap).

Figure 2:
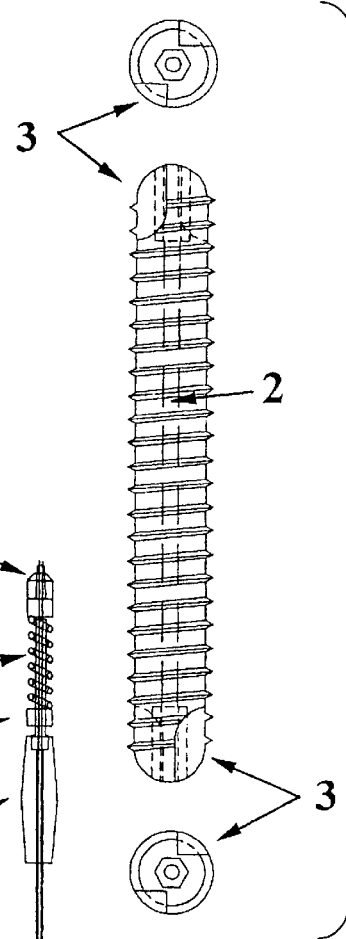
FIG. 2 is illustrative of the embodiment of the implanted axial intramedullary screw shown in FIG. 1.

(2). Two-wayness is the second distinguishing characteristic of AIMS. The screw may be hollow in the central part (FIG. 2, reference numeral 2) or not, with two-way self-tapping tips and thread cutters (FIG. 2, reference numeral 3). On both sides there is also a screwdriver connection (sextant imbus, transverse or cruciate, Phillips, Torx etc.). Because of the two-wayness, the operative procedure may begin retrogradely through the fracture gap from inside, and then, by the use of the hollow screwdriver over the guiding Kirschner wire, it will be returned from outside.

(3). The central hollow of the AIMS may vary between 0.5 and 5–10 mm according to its diameter. As well as the formerly mentioned guiding function, the Kirschner wire or wire cable may be used for axial static compression between two bone parts (proximal and distal). For this function there is a fastener composed of the compression spring with threaded hollow rod (inside the spring) connected to the back of the screwdriver with the Kirschner wire attachment (FIG. 3, reference numeral 5).

(4). The connection of AIMS by the thread to the internal cortical part of the long tubular bone creates a very high degree of axial stability among the fractured parts. It is sufficient in some types of fractures.

(5). However, it is possible to lock the AIMS by transversely applied screws in any directions by which additional rotatory stability is obtained (in intrarticular fractures or in those in metaphyseal areas).

Figure 9:
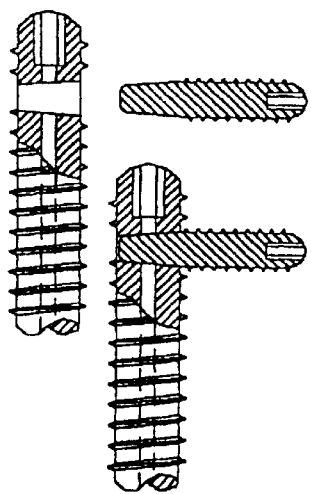
Figure 10:
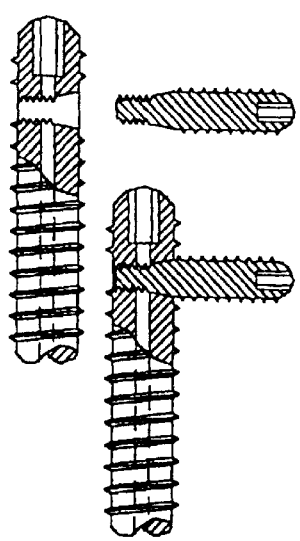
Figure 11:
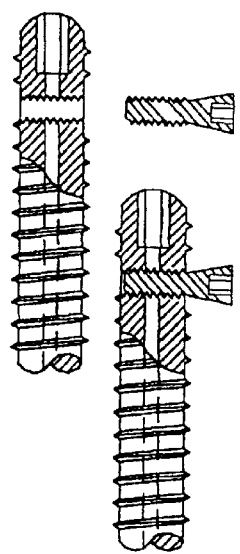
Figure 12A:
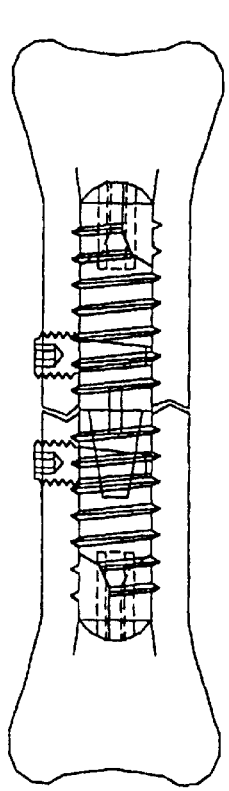
FIGS. 12A and 12B are illustrative of a modular embodiment of an axial intramedullary screw and transverse screws in accordance with the subject invention.

(6). In addition to an antirotational function of the transverse locking screws, it is possible also to produce compression by them between the lateral free bone fragments and centrally positioned AIMS (FIG. 11). The connection between the central AIMS and locking screw may be cylindrical (FIG. 6, reference numeral 11), conical (FIG. 8, reference numeral 12; FIG. 9, and FIG. 12, reference numeral 17) unloading (neutral) screw (FIG. 10) and compression screw (FIG. 11). Each of these connections may approach the central AIMS perpendicularly or with some angle to it (FIGS. 8–13). Selection depends on the local biomechanical needs and this contributes to more operative possibilities for free bone fragment stabilization.

Figure 1:
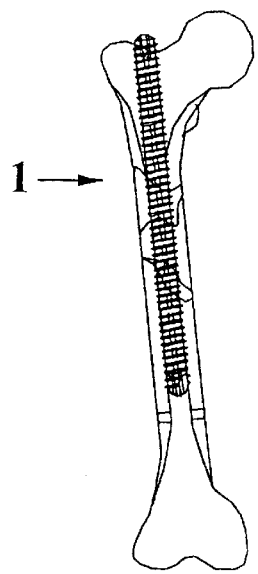
FIG. 1 is illustrative of a fractured bone including an axial intramedullary screw implanted therein in accordance with the subject invention.
Figures 5, 6, 7, 8:
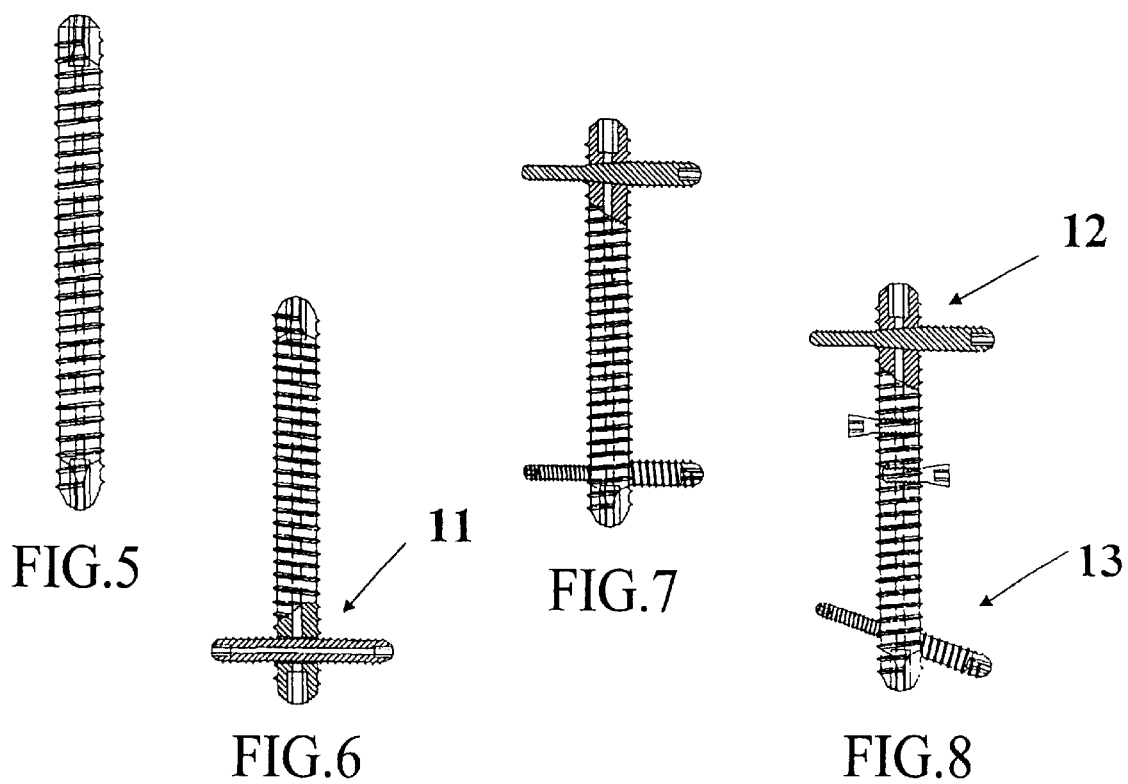
FIGS. 5–11 are illustrative of variations of an axial intramedullary screw and one or more transverse screws in accordance with the subject invention.

Using the AO/ASIF classification of fractures as ABC types (Comprehensive Classification of Fractures of Long Bones, M. E. Mueller; M. Allgower, R. Schneider, H. Willenegger; Manual of Internal Fixation, Third Edition, Springer Verlag 1991), we can easy recognize a practical concordance with classification of AIMS. In practice we may use three types of AIMS:

(1). Simple AIMS (FIG. 1, FIG. 3, FIG. 5). These are applicable for all fractures of type A (1, 2 and 3) in the diaphyseal parts of long bones.

(2). Interlocking AIMS
  (a) One-sided (FIG. 10, FIG. 11, FIG. 12). These are applicable for all fractures of type B (1, 2 and 3) in the diaphyseal parts of long bones where is a need for additional fixation of a free bone fragment (FIG. 1, reference numeral 1). These are also applicable in some cases of intrarticular fractures of type B (1, 2 and 3);
  (b) Two-sided (FIG. 4, FIG. 6, FIG. 7). These are applicable for all fractures of type A (1, 2 and 3) in distal parts of long bones and in intrarticular fractures type C (1, 2 and 3);
  (c) Unipolar (FIG. 6);
  (d) Bipolar (FIG. 7). These are applicable for all diaphyseal fractures of type C (1, 2 and 3) and in distal parts of long bones for intrarticular fractures of type C (1, 2 and 3);

(e) Combined—multiple and many-sided (FIG. 8) are variable and composed of all formerly mentioned combinations. They are applicable mainly for complex fractures of type C. Transverse interlocking screws may approach the central AIMS by different angles.

Figure 12B:
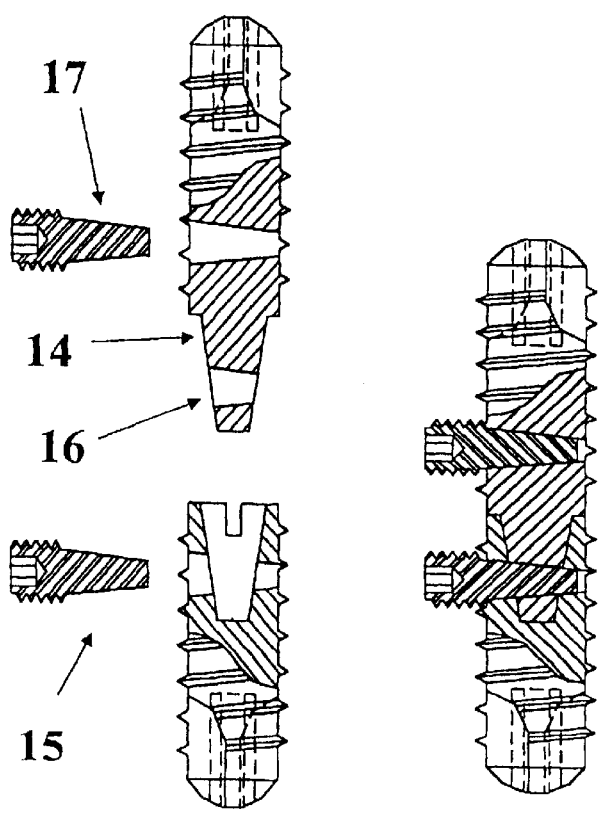

(3). Modular AIMS (twofold and threefold) is specially applicable for treatment of fractures on small metacarpal and metatarsal bones or in come cases of fractures in growing bones in children (for prevention of injury of the growth plate). With each part of this modular AIMS it is possible to screw in both directions. It is characterized by an axial conical connection between them (FIG. 12, reference numeral 14) and compression of the bone segments is induced over an axially-positioned additional transverse conical connection-interlocking screw (FIG. 12, reference numeral 15) through the hole of the axial conus (FIG. 12, reference numeral 16). The additional conical interlocking screw functions in derotation stability (FIG. 12B, reference numeral 17).

Two methods of operative procedure may be applied in the application of the AIMS system: namely, (1) In a retrograde way through the fracture gap from inside, and then by the use of a hollow screwdriver over the guiding Kirschner wire AIMS will be returned from outside bridging the fracture (FIG. 3); and (2) In an antigrade way identical to the Kuntscher or Rush nail procedure of implantation through the great trochanter of the femur or major tubercule of the humerus. These AIMS may enter the bone from outside. They may possess a head or be without, or they may be hollow or solid. They are very similar in form to standard (ISO) cortical or spongious screws although their size is much bigger.

AIMS is applicable to human bone surgery and also in veterinary surgery for large animals (horses etc.) and small animals (dogs, cats, birds etc.) There are thus great variations in sizes and the diameter of AIMS may vary according to the internal diameter of the cortices of long bones ( 1–18 mm), and in length from 20–500 mm.

Figures 3A, 3B, 3C, 3D, 3E:
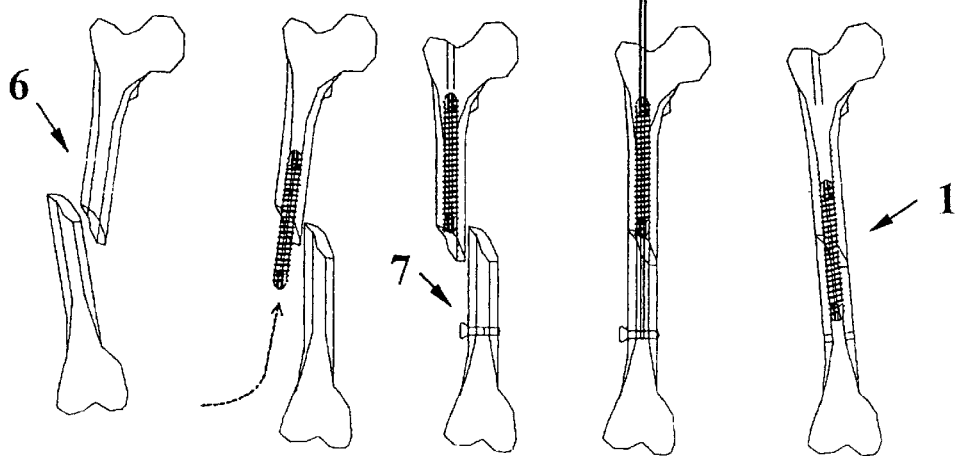
FIGS. 3A–3E are illustrative of the surgical procedure for implanting the screw shown in FIG. 2 into a fractured bone as shown in FIG. 1.
Figures 4A, 4B, 4C:
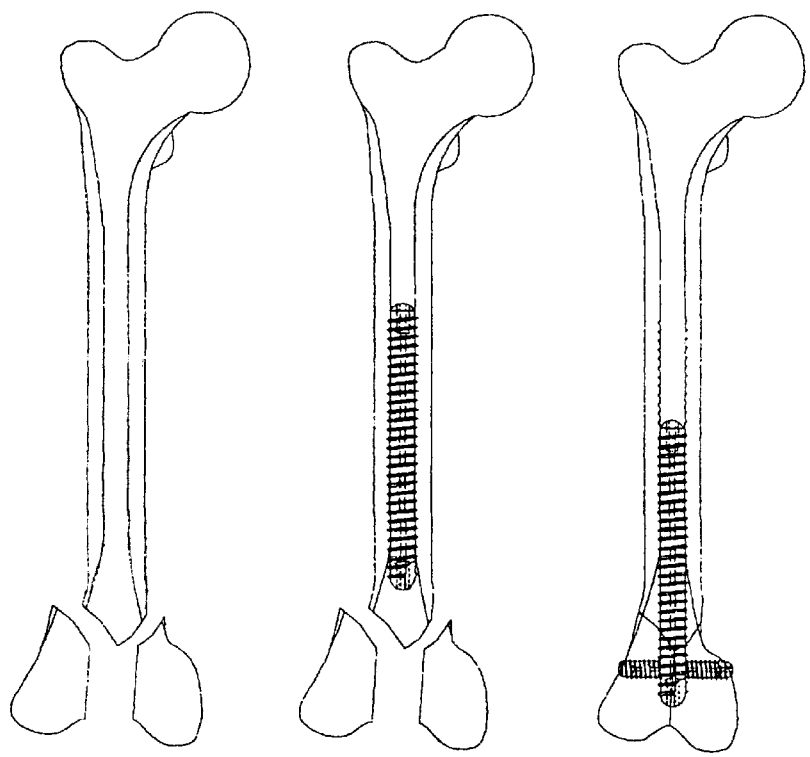
FIGS. 4A–4C are illustrative of a surgical procedure where bone fragments are stabilized with an axial intramedullary screw and a transverse screw in accordance with a second embodiment of the subject invention.

An operative procedure begins through a standard approach to open reposition (FIG. 3A). Then follows drilling a proximal hole through the great trochanter of the femur (or major tubercle of the humerus, or proximal tibia etc.) retrogradely from inside to outside (FIG. 3B). In the distal bone part, a guiding and compressing Kirschner wire or wire cord is attached to a single cortical screw (FIG. 3C). This is followed with retrograde application of AIMS to the proximal bone fragment over the attached wire (AIMS and screwdriver are hollow). After repositioning of the fractured parts, compression is made by the Kirschner wire with a compressive screw nut (FIG. 3D). Then follows screwing the AIMS over the fractured area to the distal fragment (FIG. 3E).

The materials in which AIMS may be produced are standard stainless steel for implants ISO 5832/6 5832/IV or 5832-8, or titanium for implants ISO 5832-3. A very important type of AIMS is produced from resorptive implant materials (polyglucoside, polylactide, PDS etc.). Such resorptive types are in the same form as the formerly described metallic AIMS, and they are very practical for young people and children in the treatment of fractures or corrective osteotomies for hip dysplasia or other deformities. The same applies to veterinary surgery.

The foregoing detailed description merely illustrates the principles of the invention. It will thus be appreciated that those skilled in the art will be able to devise various arrangements which, although not explicitly described or shown herein, embody the principles of the invention and are thus within its spirit and scope.

What is claimed is:

1. Axial intramedullary screw for the operative treatment of fracture of long bones in human or veterinary bone surgery, wherein said screw comprises two tips and an outer surface, said outer surface being provided with a screw thread extending along substantially its entire length, and wherein said screw comprises, at each of said tips, a connection portion for a screwdriver.

2. Axial intramedullary screw according to claim 1, wherein said connection portion at said tips is selected among the shapes of imbus—sextant, transverse or cruciate connection, Phillips or Torx.

3. Axial intramedullary screw according to claim 1, wherein self-tapping tips are provided at each tip thereof.

4. Axial intramedullary screw according to claim 1, wherein said screw is hollow centrally along its entire length, said hollow centre having a dimension between 0.5 mm and 10 mm for the purpose of guiding Kirschner wires or wire cord.

5. Axial intramedullary screw according to claim 1, wherein said screw is substantially solid between the connection portions at its tips.

6. Axial intramedullary screw according to claim 1, wherein at least one transverse hole is provided in said screw.

7. Axial intramedullary screw according to claim 6, wherein a plurality of transverse holes are provided in said screw.

8. Axial intramedullary screw according to claim 7, wherein said screw has a longitudinal axis, said transverse holes being arranged at different angles with respect to said longitudinal axis.

9. Axial intramedullary screw according to claim 6, wherein said at least one transverse hole is cylindrical.

10. Axial intramedullary screw according to claim 6, wherein said at least one transverse hole is conical.

11. Axial intramedullary screw according to claim 9, wherein said at least one transverse hole is threaded.

12. Axial intramedullary screw according to claim 11, wherein said at least one transverse hole is further provided with a conical non-threaded portion at the start of said hole for receiving a conical portion of a transverse screw.

13. Axial intramedullary screw according to claim 1, wherein said screw is formed by two-fold or three-folded threaded modular sections, each of said modular sections being joined to an adjacent section by means of conical mating portions, said conical mating portions being further provided with a conical transverse hole portion for receiving a portion of a conical interlocking transverse screw, so as to provide compression and rotation prevention.

14. A screw as claimed in claim 1, wherein the screw is made of stainless steel for bone implants ISO 58532/6 or ISO 5832/IV or 5832-8 or titanium ISO 5832-3.

15. A screw as claimed in claim 1, wherein the screw is made of resorptive material for bone implants.

16. Axial intramedullary screw according to claim 1, wherein said outer surface is substantially straight and cylindrical.

17. Method of treating fractures in long bones in human or veterinary bone surgery, wherein said fracture comprises a first bone part with an intramedullary channel having a first fracture surface and at least one second bone part having a second fracture surface, the method comprising the steps of screwing a screw including a threaded outer surface in a first axial direction into and along said intramedullary channel whereby screw threads of said threaded outer surface cut into cortical bone, placing said first and said second fracture surfaces into a mating position, then screwing said screw in a second axial direction opposite to said first axial direction into said at least one second bone part to thereby join said first bone part and said at least one second bone part.

18. Method according to claim 17, wherein screwing in said second axial direction causes threads of said screw to cut into cortical bone of said at least one second bone part.

19. Method according to claim 17, wherein said screw has a longitudinal axis and wherein transverse screws are passed through an outer surface of at least one of said bone parts into bored holes extending transversely through said longitudinal axis.

* * * * *